United States Patent
Ljungquist

(12) 
(10) Patent No.: US 6,708,847 B2
(45) Date of Patent: Mar. 23, 2004

(54) DISPENSER FOR MIXING THEN DISPENSING MULTIPLE COMPONENTS

(75) Inventor: Olle Ljungquist, Vallentuna (SE)

(73) Assignee: Biovitrum AB (SE)

( * ) Notice: Subject to any disclaimer, the term of this patent is extended or adjusted under 35 U.S.C. 154(b) by 41 days.

(21) Appl. No.: 10/185,975

(22) Filed: Jun. 27, 2002

(65) Prior Publication Data

US 2003/0071063 A1 Apr. 17, 2003

(30) Foreign Application Priority Data

Jun. 27, 2001 (SE) .................................................. 0102288

(51) Int. Cl.⁷ ................................................. B67D 5/52
(52) U.S. Cl. ..................... 222/137; 222/145.5; 222/392
(58) Field of Search .............................. 222/137, 145.5, 222/145.6, 386, 391, 392, 459

(56) References Cited

U.S. PATENT DOCUMENTS

| | | | | | |
|---|---|---|---|---|---|
| 2,240,046 | A | * | 4/1941 | Marra | 222/391 |
| 3,774,809 | A | * | 11/1973 | Bratton | 222/137 |
| 4,957,223 | A | * | 9/1990 | Beilush | 222/340 |
| 4,979,942 | A | * | 12/1990 | Wolf et al. | 604/83 |
| 5,290,259 | A | * | 3/1994 | Fischer | 604/218 |

* cited by examiner

*Primary Examiner*—Joseph A. Kaufman
(74) *Attorney, Agent, or Firm*—Fish & Richardson P.C.

(57) ABSTRACT

A dispenser comprising at least two parallel, hollow cylinders for supplying different mutually reactive components to a mixing device located downstream of the cylinders. The dispenser comprises a respective first piston moveable in each of the cylinders and displaceable by a piston rod connected to the respective piston. A component for actuating the pistons rods to perform a forward stroke of the pistons in their respective cylinders for dispensing an amount of the reactive components to the mixing device comprises at least one rotatable member biased in a rotational direction by a torsion spring, and at least one flexible string attached to the rotatable member and to an element connected to the piston rods. A manually operable brake member is arranged to normally act on the rotatable member to hold it still, but, when deactivated, adapted to release the rotatable member thereby causing the pistons to dispense the reactive components to the mixing device.

21 Claims, 2 Drawing Sheets

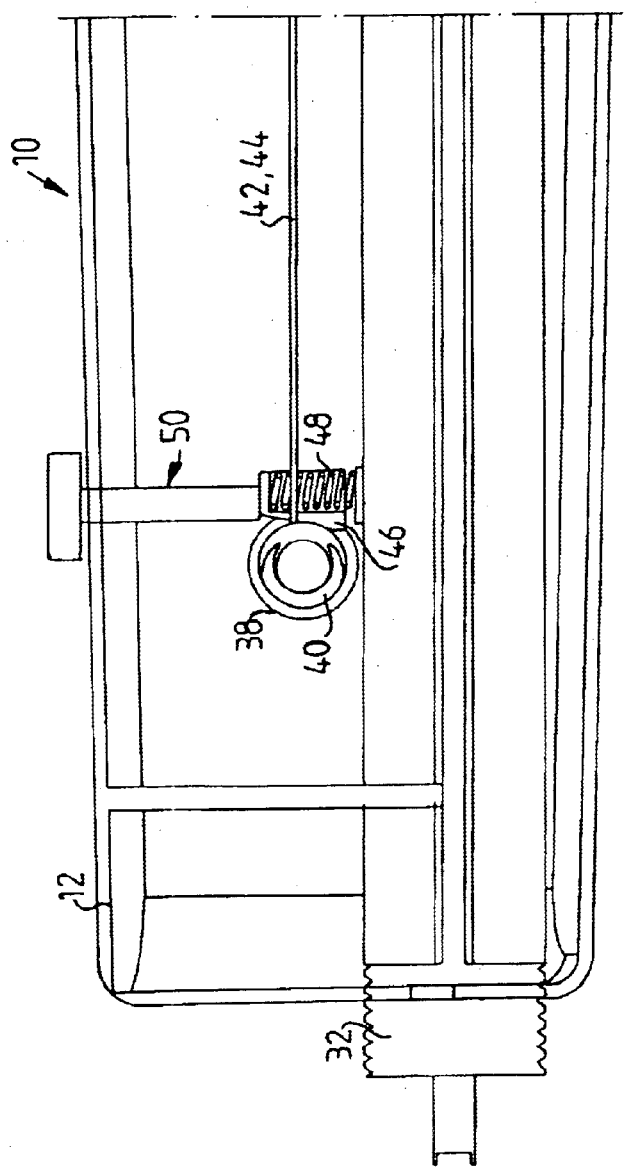
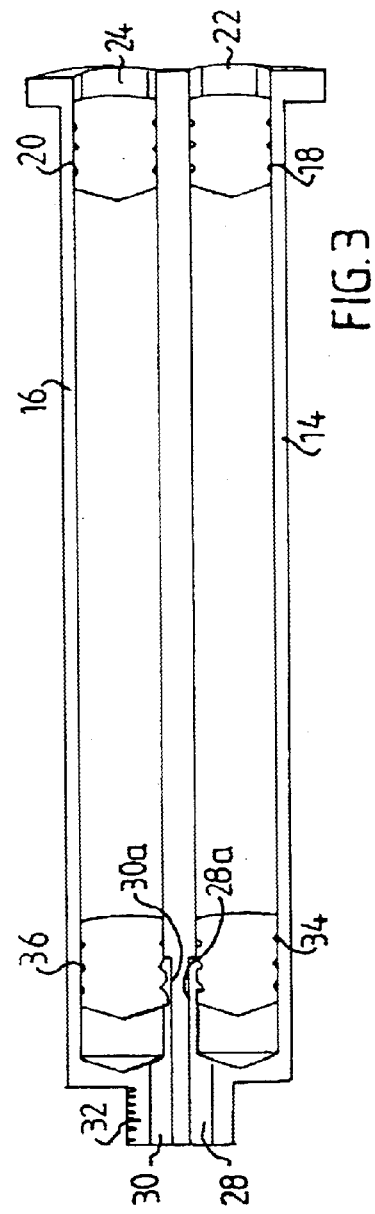

DISPENSER FOR MIXING THEN DISPENSING MULTIPLE COMPONENTS

CROSS REFERENCE TO RELATED APPLICATION

This application claims priority from Swedish Patent Application No. 0102288-8, filed Jun. 27, 2001, the entire content of which is incorporated herein by reference.

FIELD OF THE INVENTION

The present invention relates in general to a dispenser comprising at least two parallel, hollow cylinders for supplying different mutually reactive components to a mixing device located downstream of said cylinders; a respective first piston moveable in each of the cylinders and displaceable by a piston rod connected to the respective piston; said pistons rods being interconnected for simultaneous dispensing of the components contained in the cylinders, when the piston rods and pistons are displaced in the cylinders towards a respective outlet therein; and a means for actuating the pistons rods to perform a forward stroke of the pistons in their respective cylinders for dispensing an amount of said reactive components to the mixing device, said actuating means comprising a spring member adapted to act on the piston rods, and a manually operable brake member for controlling the force of the spring acting on the piston rods.

In particular, but not exclusively, the present invention relates to a dispenser of the above mentioned kind for supplying two mutually reactive sealant components, such as fibrinogen and thrombin, to a mixing device for applying an accurately mixed solution of such components to biological tissue, for example for effecting hemostasis or for any other type of therapeutic objective.

BACKGROUND OF THE INVENTION

Various types of dispensers for dispensing a two-component fluid mixture are known. For example, WO 98/40115 discloses a dispenser of the kind mentioned in the introductory portion above. The dispenser has the shape of a pistol with a handle at the rear end thereof. A compression coil spring acts on the rear part of the piston rods via a slide, and one arm of a two-armed lever mounted at the handle acts as a brake on the slide to control the spring force exerted on the piston rods to thereby control the discharge of the fluid contents in the containers. Although this pistol-shaped dispenser is mechanically simple, it may in some instances be awkward and difficult to manipulate accurately, when a precise application of the dispensed fluid mixture is required.

SUMMARY OF THE INVENTION

It is an object of the present invention to provide a dispenser, which is very compact in size and easy to manipulate carefully and accurately in narrow spaces. The dispenser is preferably designed to be hand-held like a pencil with easy finger access to a brake-deactivating knob and may be disposable or refilled after emptying of the cylinder contents.

For this purpose the dispenser of the present invention, as described above by way of introduction, is characterized in that the actuating means comprises at least one rotatable member biased in a rotational direction by a torsion spring, and at least one flexible string attached, at a first end thereof, to the rotatable member so as to be wound thereon, and, at a second end thereof, to an element connected to the piston rods, wherein the manually operable brake means is arranged to normally act on the rotatable member to hold it still, but, when deactivated, adapted to release the rotatable member to thereby wind the string upon the rotatable member while simultaneously causing the pistons to perform a forward stroke for dispensing the reactive components to the mixing device.

Other features and structural details of the dispenser of the present invention will be set forth in the dependent claims and described in the following description under reference to the accompanying drawings.

Unless otherwise defined, all technical and scientific terms used herein have the same meaning as commonly understood by one of ordinary skill in the art to which this invention belongs. Suitable methods and materials are described below, although methods and materials similar or equivalent to those described herein can also be used in the practice or testing of the present invention. All publications, patent applications, patents, and other references mentioned herein are incorporated by reference in their entirety. In case of conflict, the present specification, including definitions, will control. In addition, the materials, methods, and examples are illustrative only and not intended to be limiting.

BRIEF DESCRIPTION OF THE DRAWINGS

FIG. 2 is a side view of a front portion of the dispenser in FIG. 1.

FIG. 3 is a schematic side view of two cylinder compartments containing two mutually reactive fluid components in the dispenser of the present invention.

DESCRIPTION OF A PREFERRED EMBODIMENT

Figure 1:
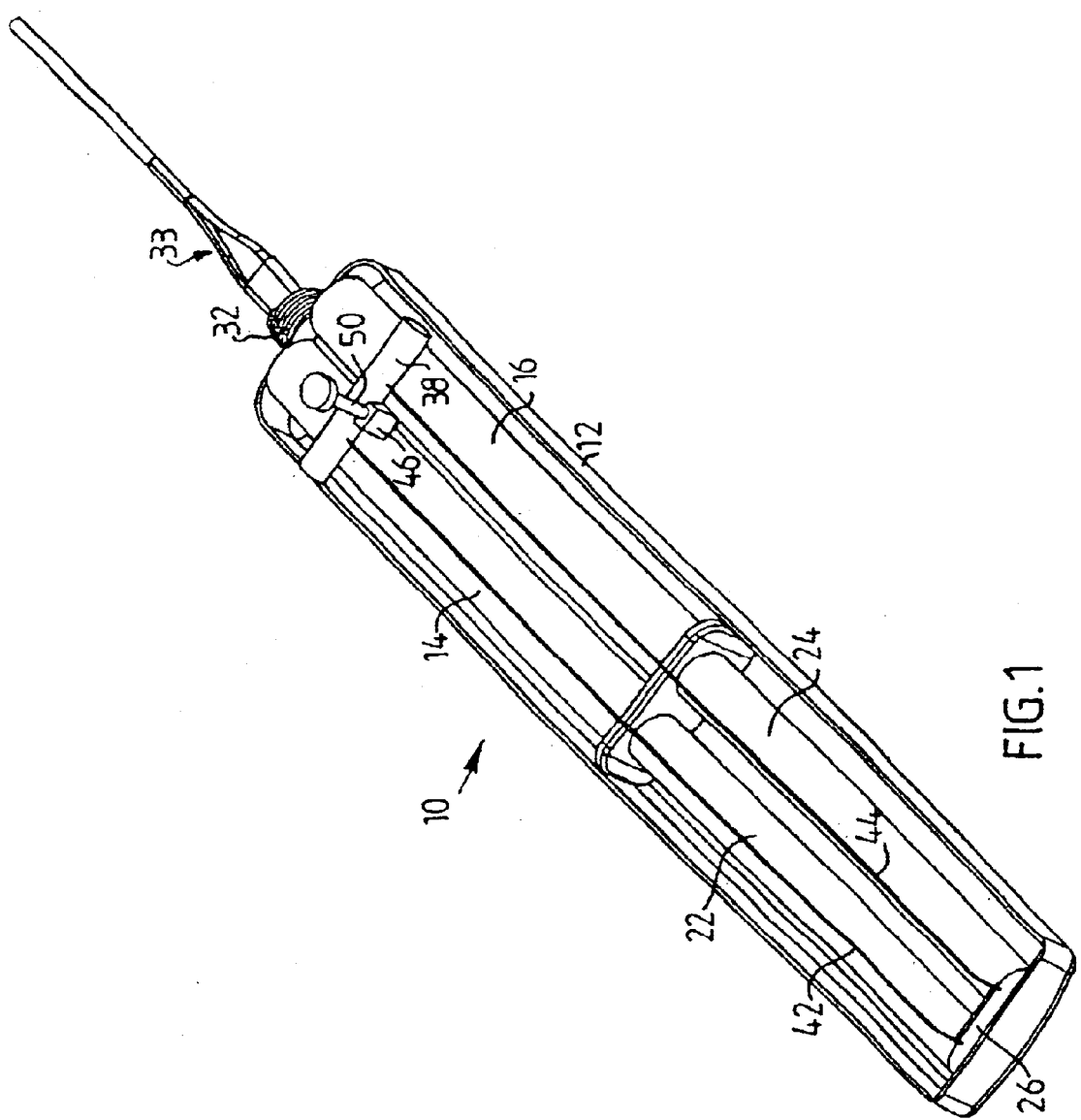
FIG. 1 is a perspective view of a dispenser according to the present invention with a cover taken away.

As shown in FIG. 1, a dispenser 10 of the present invention for dispensing two mutually reactive components, such as fibrinogen and thrombin to be mixed for creating a sealant for medical use, comprises an oblong housing 12 for receiving therein two parallel cylinders 14, 16 containing the two reactive fluid components. A first, rear piston 18, 20 is moveable forwardly in its respective cylinder 14, 16 from an initial rear position (FIG. 3), in which the cylinders 14, 16 are fully filled, by means of a respective piston rod 22, 24 extending rearwardly a distance corresponding at least to the intended maximal forward stroke of the pistons 18, 20 in the cylinders 14, 16. The piston rods 22, 24 are interconnected by a plate member 26 at a rear end thereof so as to be able of performing a simultaneous forward displacement of the pistons 18, 20 in the cylinders to thereby simultaneously discharge the two fluid components through respective outlet channels 28, 30 extending through a common frontal hub portion 32. A mixing appliance 33, for example of the kind described in SE-A-0100091-8, may be detachably mounted to the hub portion 32, as shown in FIG. 1.

As shown in FIG. 3, a forward piston 34, 36 is, in an initial rear position thereof in the respective cylinder, blocking the outlet channels 28, 30 for sealing the content in the cylinders before the initial use. Upon an initial forward displacement of the first, rear pistons 18, 20 in the cylinders the forward sealing pistons 34, 36 will be moved to a forward position in which they allow for a free fluid communication between the outlet channels 28, 30 and the interior of the cylinders 14, 16 via a bypass 28a and 30a.

Furthermore, the dispenser 10 of the present invention has a new type of actuating device for simultaneously displacing the pistons 18, 20 in their respective cylinders 14, 16. The actuating device comprises a rotatable drum 38 journalled for rotation about an axis transverse to the longitudinal extension of the dispenser 10 at a front portion of the housing 12. The drum 38 is biased by a torsion spring, schematically indicated at 40 in FIG. 2, so as to be capable of winding up at least one cord or string 42, 44 connected to the plate member 26 at the rear end of the piston rods 22, 24 of the respective cylinder 14, 16. A brake shoe 46 is normally frictionally engaging the drum 38 for preventing rotation thereof by means of a compression spring 48 biasing the shoe 46. The brake shoe 46 may be disengaged from the drum 38 by depressing a push rod 50 against the action of the spring 48 thereby allowing the torsion spring 40 to rotate the drum 38 for winding up the cords 42, 44 thereon and hence causing the first pistons 18, 20 to perform a forward movement in the cylinders 14, 16 for dispensing a desired amount of the respective reactive fluid components to the mixing appliance 33. As described above, the initial displacement of the first pistons 18, 20 will first cause the forward pistons 34, 36 to move from a sealing position to a forward position in which they open up the fluid communication between the outlet channels 28, 30 and the interior of the cylinders 14, 16 via the bypasses 28a, 30a.

The above-described dispenser 10 is structurally simple and compact and is easy to manipulate for accurate application of a mixed composition to an object owing to the fact that the dispenser may be hand-held in the vicinity of the outlet end thereof while at the same time controlling the discharge of the composition by depressing the push rod 50 with e.g. the thumb.

OTHER EMBODIMENTS

It is to be understood that, while the invention has been described in conjunction with the detailed description thereof, the foregoing description is intended to illustrate and not limit the scope of the invention. Other aspects, advantages, and modifications of the invention are within the scope of the claims set forth below.

What is claimed is:

1. A dispenser comprising:
   at least two parallel, hollow cylinders for supplying different mutually reactive components to a mixing device located downstream of said cylinders;
   a respective first piston moveable in each of the cylinders and displaceable by a piston rod connected to the respective piston;
   said pistons rods being interconnected for simultaneous dispensing of the components contained in the cylinders, when the piston rods and pistons are displaced in the cylinders towards a respective outlet therein; and
   a means for actuating the pistons rods to perform a forward stroke of the pistons in their respective cylinders for dispensing an amount of said reactive components to the mixing device,
   said actuating means comprising a spring member adapted to act on the piston rods, and a manually operable brake member for controlling the force of the spring acting on the piston rods, wherein said actuating means further comprises:
   at least one rotatable member biased in a rotational direction by a torsion spring, and
   at least one flexible string attached, at a first end thereof, to the rotatable member so as to be wound thereon, and at a second end thereof to an element connected to the piston rods, wherein the manually operable brake member is arranged to normally act on the rotatable member to hold it still, but, when deactivated, adapted to release the rotatable member to thereby wind the string upon the rotatable member while simultaneously causing the pistons to perform a forward stroke for dispensing the reactive components to the mixing device.

2. The dispenser of claim 1, wherein the brake member and the rotatable member are located in the vicinity of a forward end of the cylinders, and that the rotatable member is journalled so as to be able to rotate about an axis transverse to a longitudinal extension of the cylinders.

3. The dispenser of claim 2, wherein the brake member comprises a brake shoe biased by a spring to normally frictionally engage the rotatable member to a locked position, said brake shoe being moveable against the action of said spring by means of a rod provided with a push button so as to release the rotatable member and allowing it to rotate and perform a pulling action on the piston rods by means of the string.

4. The dispenser of claim 1, wherein the cylinders and the piston rods protruding from a rear end of the cylinders are accommodated in a common oblong housing.

5. The dispenser of claim 2, wherein the cylinders and the piston rods protruding from a rear end of the cylinders are accommodated in a common oblong housing.

6. The dispenser of claim 3, wherein the cylinders and the piston rods protruding from a rear end of the cylinders are accommodated in a common oblong housing.

7. The dispenser of claim 1, wherein each cylinder, at a forward end thereof, houses a second piston, which in a fully filled state of the respective cylinder seals the outlet thereof, and which upon an initial displacement of the respective first piston opens a bypass channel thereby bringing the interior of the cylinder into fluid communication with said outlet.

8. The dispenser of claim 2, wherein each cylinder, at a forward end thereof, houses a second piston, which in a fully filled state of the respective cylinder seals the outlet thereof, and which upon an initial displacement of the respective first piston opens a bypass channel thereby bringing the interior of the cylinder into fluid communication with said outlet.

9. The dispenser of claim 3, wherein each cylinder, at a forward end thereof, houses a second piston, which in a fully filled state of the respective cylinder seals the outlet thereof, and which upon an initial displacement of the respective first piston opens a bypass channel thereby bringing the interior of the cylinder into fluid communication with said outlet.

10. The dispenser of claim 4, wherein each cylinder, at a forward end thereof, houses a second piston, which in a fully filled state of the respective cylinder seals the outlet thereof, and which upon an initial displacement of the respective first piston opens a bypass channel thereby bringing the interior of the cylinder into fluid communication with said outlet.

11. The dispenser of claim 5, wherein each cylinder, at a forward end thereof, houses a second piston, which in a fully filled state of the respective cylinder seals the outlet thereof, and which upon an initial displacement of the respective first piston opens a bypass channel thereby bringing the interior of the cylinder into fluid communication with said outlet.

12. The dispenser of claim 6, wherein each cylinder, at a forward end thereof, houses a second piston, which in a fully filled state of the respective cylinder seals the outlet thereof, and which upon an initial displacement of the respective first piston opens a bypass channel thereby bringing the interior of the cylinder into fluid communication with said outlet.

13. The dispenser of claim 4, wherein the outlets of the cylinders extend through a common hub at the front end of the housing.

14. The dispenser of claim 5, wherein the outlets of the cylinders extend through a common hub at the front end of the housing.

15. The dispenser of claim 6, wherein the outlets of the cylinders extend through a common hub at the front end of the housing.

16. The dispenser of claim 7, wherein the outlets of the cylinders extend through a common hub at the front end of the housing.

17. The dispenser of claim 8, wherein the outlets of the cylinders extend through a common hub at the front end of the housing.

18. The dispenser of claim 9, wherein the outlets of the cylinders extend through a common hub at the front end of the housing.

19. The dispenser of claim 10, wherein the outlets of the cylinders extend through a common hub at the front end of the housing.

20. The dispenser of claim 11, wherein the outlets of the cylinders extend through a common hub at the front end of the housing.

21. The dispenser of claim 12, wherein the outlets of the cylinders extend through a common hub at the front end of the housing.

* * * * *

UNITED STATES PATENT AND TRADEMARK OFFICE
CERTIFICATE OF CORRECTION

PATENT NO. : 6,708,847 B2  Page 1 of 1
DATED : March 23, 2004
INVENTOR(S) : Olle Ljungquist It is certified that error appears in the above-identified patent and that said Letters Patent is hereby corrected as shown below:

Title page,
Item [30], Foreign Application Priority Data, replace "0102288" with -- 0102288-8 --
Item [56], References Cited, U.S. PATENT DOCUMENTS, insert:
-- 5,116,315 (Capozzi et al.)
 5,520,658 (Holm)
 5,975,367 (Coelho et al.)
 6,047,861 (Vidal et al.)
 6,223,936 B1 (Jeanbourquin) --; and
FOREIGN PATENT DOCUMENTS, insert:
-- EP 0 858 775 A1 --

Signed and Sealed this

Twenty-fourth Day of August, 2004

JON W. DUDAS
*Director of the United States Patent and Trademark Office*